United States Patent
Onikubo et al.

(10) Patent No.: US 12,193,642 B2
(45) Date of Patent: Jan. 14, 2025

(54) ENDOSCOPE SYSTEM, NON-TRANSITORY COMPUTER READABLE MEDIUM, AND METHOD

(71) Applicant: Sony Group Corporation, Tokyo (JP)

(72) Inventors: Masatoshi Onikubo, Tokyo (JP); Takashi Kawai, Tokyo (JP); Yoshito Terashima, Tokyo (JP); Yoshikazu Oochi, Tokyo (JP)

(73) Assignee: Sony Group Corporation, Tokyo (JP)

( * ) Notice: Subject to any disclaimer, the term of this patent is extended or adjusted under 35 U.S.C. 154(b) by 576 days.

(21) Appl. No.: 17/440,799

(22) PCT Filed: Mar. 27, 2020

(86) PCT No.: PCT/JP2020/014172
§ 371 (c)(1),
(2) Date: Sep. 20, 2021

(87) PCT Pub. No.: WO2020/196868
PCT Pub. Date: Oct. 1, 2020

(65) Prior Publication Data
US 2022/0167837 A1      Jun. 2, 2022

(30) Foreign Application Priority Data
Mar. 27, 2019  (JP) ................... 2019-060221

(51) Int. Cl.
*A61B 1/00*   (2006.01)
*A61B 1/04*   (2006.01)

(52) U.S. Cl.
CPC ...... *A61B 1/00188* (2013.01); *A61B 1/00006* (2013.01); *A61B 1/00045* (2013.01); *A61B 1/00149* (2013.01); *A61B 1/04* (2013.01)

(58) Field of Classification Search
CPC ............ A61B 1/00188; A61B 1/00006; A61B 1/00045; A61B 1/00149; A61B 1/04;
(Continued)

(56) References Cited

U.S. PATENT DOCUMENTS

2007/0225550 A1* 9/2007 Gattani ................. A61B 90/37
                                                          600/101
2012/0289782 A1* 11/2012 Viola .................. A61B 1/00193
                                                          600/111
(Continued)

FOREIGN PATENT DOCUMENTS

EP    2 716 207 A1    4/2014
JP    2005130962 A    5/2005
(Continued)

OTHER PUBLICATIONS

International Search Report and Written Opinion mailed on Jul. 22, 2020, received for PCT Application PCT/JP2020/014172, Filed on Mar. 27, 2020, 11 pages.

*Primary Examiner* — Timothy J Neal
*Assistant Examiner* — James Edward Boice
(74) *Attorney, Agent, or Firm* — XSENSUS LLP

(57) ABSTRACT

An endoscope system includes circuitry configured to monitor a characteristic of an endoscope including an imaging device and a scope coupled to the imaging device, wherein the characteristic is indicative of whether the scope is inserted in a living body or not, in the event that the characteristic satisfies a predetermined condition, control a focus of the endoscope system in a first manner and, in the event that the characteristic does not satisfy the predetermined condition, control the focus of the endoscope system in a second manner, different from the first manner.

20 Claims, 10 Drawing Sheets

(58) Field of Classification Search
CPC . A61B 1/00009; A61B 1/00057; A61B 34/30; A61B 2034/2019
USPC .................................................. 600/117, 167
See application file for complete search history.

(56) References Cited

U.S. PATENT DOCUMENTS

| | | | | |
|---|---|---|---|---|
| 2013/0053643 | A1* | 2/2013 | Yoshida ................. | A61B 1/126 600/114 |
| 2014/0111628 | A1* | 4/2014 | Yoshino ................... | A61B 1/05 348/65 |
| 2019/0008367 | A1* | 1/2019 | Ishikawa .............. | A61B 90/361 |
| 2020/0069149 | A1* | 3/2020 | Yanagihara ............ | G02B 23/24 |

FOREIGN PATENT DOCUMENTS

| | | |
|---|---|---|
| JP | 2011139760 A | 7/2011 |
| JP | 2013061618 A | 4/2013 |
| JP | 2015123293 A | 7/2015 |
| WO | WO-2016088186 A1 | 6/2016 |
| WO | 2017/010157 A1 | 1/2017 |
| WO | WO-2018116572 A1 | 6/2018 |
| WO | WO-2018163644 A1 | 9/2018 |
| WO | 2018/207537 A1 | 11/2018 |

* cited by examiner

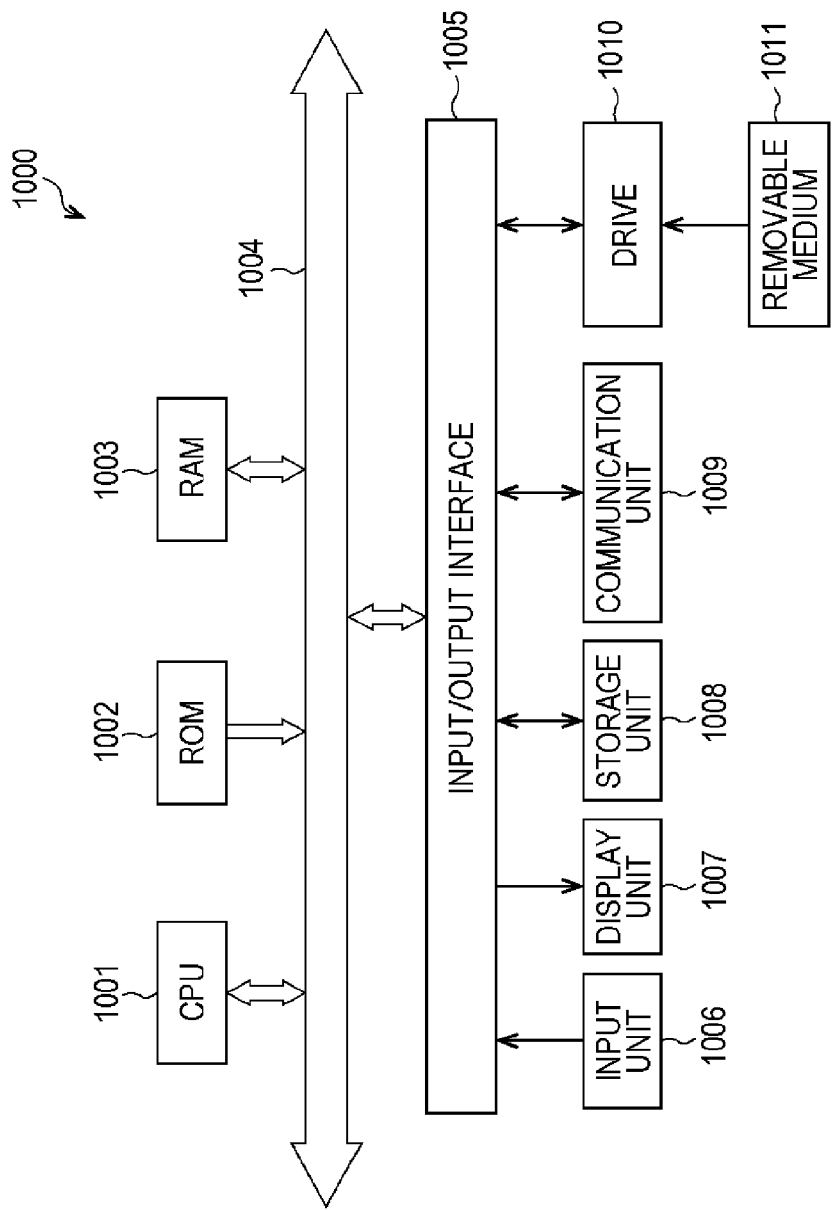

ENDOSCOPE SYSTEM, NON-TRANSITORY COMPUTER READABLE MEDIUM, AND METHOD

CROSS-REFERENCE TO RELATED APPLICATIONS

The present application is based on PCT filing PCT/JP2020/014172, filed Mar. 27, 2020, which claims priority to JP 2019-060221, filed Mar. 27, 2019, the entire contents of each are incorporated herein by reference.

TECHNICAL FIELD

The present technology relates to an endoscope system, an endoscope control method, and an imaging control device, and particularly relates to an endoscope system, an endoscope control method, and an imaging control device for use in performing auto focus (AF) when imaging inside a living body.

BACKGROUND ART

In use of a medical observation device, such as an endoscope or a microscope, the operative field often has more depth with respect to the depth of field of the medical observation device. Thus, there are cases where a certain amount of time is taken to focus on a site to be viewed. To handle this, a medical observation device having an AF function to perform automatic focusing (refer to PTL 1, for example) is proposed.

CITATION LIST

Patent Literature

PTL 1: International Publication 2017/010157

SUMMARY OF INVENTION

Technical Problem

Meanwhile, at a surgical site, an insertion part (for example, a fiber scope) connected to an imaging unit (for example, a camera head) is inserted into the living body to perform imaging via the insertion part. In this case, the insertion part is sometimes removed from the living body during the surgery, e.g., to clean blood, water droplets, dirt, or the like attached to a lens at a distal end of the insertion part. Therefore, an image greatly changes when the insertion part is inserted into the living body or removed from the living body, resulting in an unstable AF operation.

The present technology has been made in view of such a situation and is intended to achieve stable AF operation when imaging the inside of the living body.

Solution to Problem

An endoscope system according to a first aspect of the present technology includes: circuitry configured to: monitor a characteristic of an endoscope including an imaging device and a scope coupled to the imaging device, wherein the characteristic is indicative of whether the scope is inserted in a living body or not; in the event that the characteristic satisfies a predetermined condition, control a focus of the endoscope system in a first manner; and in the event that the characteristic does not satisfy the predetermined condition, control the focus of the endoscope system in a second manner, different from the first manner.

A non-transitory computer readable medium having stored thereon a program that, when executed by a computer, causes the computer to execute processing, the processing according to a second aspect of the present technology includes: monitoring a characteristic of an insertion portion that is to be inserted in and removed from a living body, the insertion portion to be connected to an image sensor that generate an image in a medical imaging system; in the event that the characteristic satisfies a predetermined condition, controlling a focus of the medical imaging system in a first manner; and in the event that the characteristic does not satisfy the predetermined condition, controlling the focus of the medical imaging system in a second manner, different from the first manner.

A method according to a third aspect of the present technology includes: monitoring a characteristic of an insertion portion that is to be inserted in and removed from a living body, the insertion portion to be connected to an image sensor that generates an image in a medical imaging system; in the event that the characteristic satisfies a predetermined condition, controlling a focus of the medical imaging system in a first manner; and in the event that the characteristic does not satisfy the predetermined condition, controlling the focus of the medical imaging system in a second manner, different from the first manner.

BRIEF DESCRIPTION OF DRAWINGS

FIG. 12 is a diagram illustrating a configuration example of a computer.

DESCRIPTION OF EMBODIMENTS

Hereinafter, embodiments of the present technology will be described. Description will be presented in the following order.

1. Embodiments
2. Modifications
3. Others

1. EMBODIMENTS

First, embodiments of the present technology will be described with reference to FIGS. 1 to 9.

<Configuration Example of Imaging System>

Figure 1:
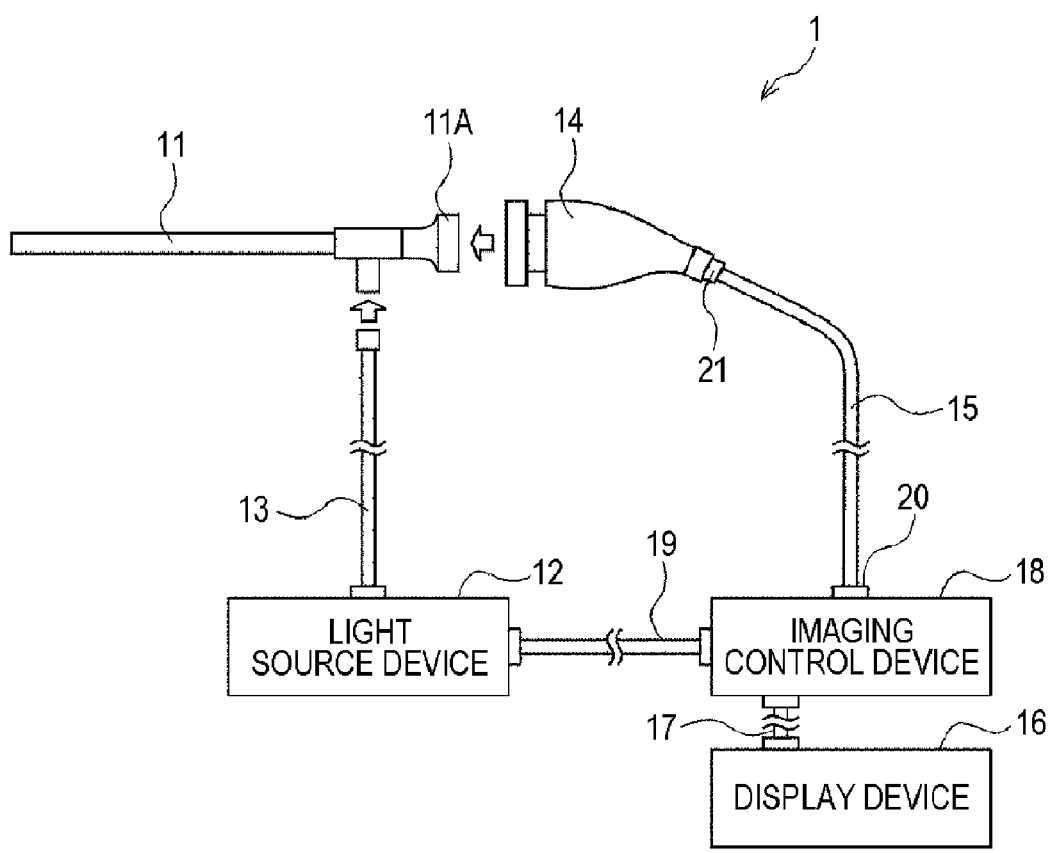
FIG. 1 is a block diagram illustrating an imaging system according to an embodiment of the present technology.

FIG. 1 illustrates a configuration example of an imaging system 1 to which the present technology is applied.

The imaging system 1 is an endoscope system used in the medical field, for example, specifically used for imaging and observation in a living body. The imaging system 1 includes an insertion part 11, a light source device 12, a light guide 13, a camera head (imaging unit) 14, a first transmission cable 15, a display device 16, a second transmission cable 17, an imaging control device 18, and a third transmission cable 19, a connector 20, and a connector 21.

For example, the insertion part 11 includes a rigid scope or a flexible scope (for example, a fiber scope). That is, the insertion part 11 is a member that is rigid or at least partially flexible and having an elongated shape so as to be inserted into the living body. The insertion part 11 includes an optical system equipped with one or more lenses to converge or focus a subject image. The insertion part 11 and the camera head 14 may be integrated with each other.

The light source device 12 is connected with a first end of the light guide 13 and provides the first end of the light guide 13 with light for illuminating the inside of the living body under the control of the imaging control device 18.

The light guide 13 is detachably connected, on a first end, to the light source device 12, and is detachably connected, on a second end, to the insertion part 11. Subsequently, the light guide 13 transmits the light supplied from the light source device 12 from the first end to the second end and supplies the light to the insertion part 11. The light supplied to the insertion part 11 is emitted from the distal end of the insertion part 11 and is directed to the inside of the living body. The light directed to the inside of the living body and reflected from inside the living body (subject image) is collected by the optical system in the insertion part 11.

The camera head 14 is detachably connected to an eyepiece unit 11A which is a proximal end of the insertion part 11. Next, under the control of the imaging control device 18, the camera head 14 captures a subject image converged by the insertion part 11, and outputs an image signal (RAW signal) generated by the imaging. An example of the image signal is an image signal of 4K or more.

Note that an image based on an image signal will be referred to as a captured image in the following.

The first transmission cable 15 is detachably connected, on a first end, to the imaging control device 18 via the connector 20, and detachably connected, on a second end, to the camera head 14 via the connector 21. Thereafter, the first transmission cable 15 transmits an image signal or the like output from the camera head 14 to the imaging control device 18, and at the same time, transmits each of a control signal, a synchronization signal, a clock signal, electric power, or the like, output from the imaging control device 18 to the camera head 14.

Note that the transmission of an image signal or the like from the camera head 14 to the imaging control device 18 via the first transmission cable 15 may use either an optical signal or an electrical signal. The also applies to transmission of the control signal, the synchronization signal, and the clock signal from the imaging control device 18 to the camera head 14 via the first transmission cable 15.

The display device 16 displays a display image based on a video signal from the imaging control device 18 under the control of the imaging control device 18.

The second transmission cable 17 is detachably connected, on a first end, to the display device 16, while detachably connected, on a second end, to the imaging control device 18. The second transmission cable 17 subsequently transmits the video signal processed by the imaging control device 18 and the control signal output from the imaging control device 18 to the display device 16.

The imaging control device 18 includes a camera control unit (CCU) and a central processing unit (CPU) or the like. The imaging control device 18 integrally controls operation of the light source device 12, the camera head 14, and the display device 16.

The third transmission cable 19 is detachably connected, at a first end, to the light source device 12, while detachably connected, at a second end, to the imaging control device 18. Subsequently, the third transmission cable 19 transmits the control signal from the imaging control device 18 to the light source device 12.

<Configuration Example of Camera Head 14, Display Device 16, and Imaging Control Device 18>

Next, configuration examples of the camera head 14, the display device 16, and the imaging control device 18 will be described with reference to FIG. 2.

Figure 2:
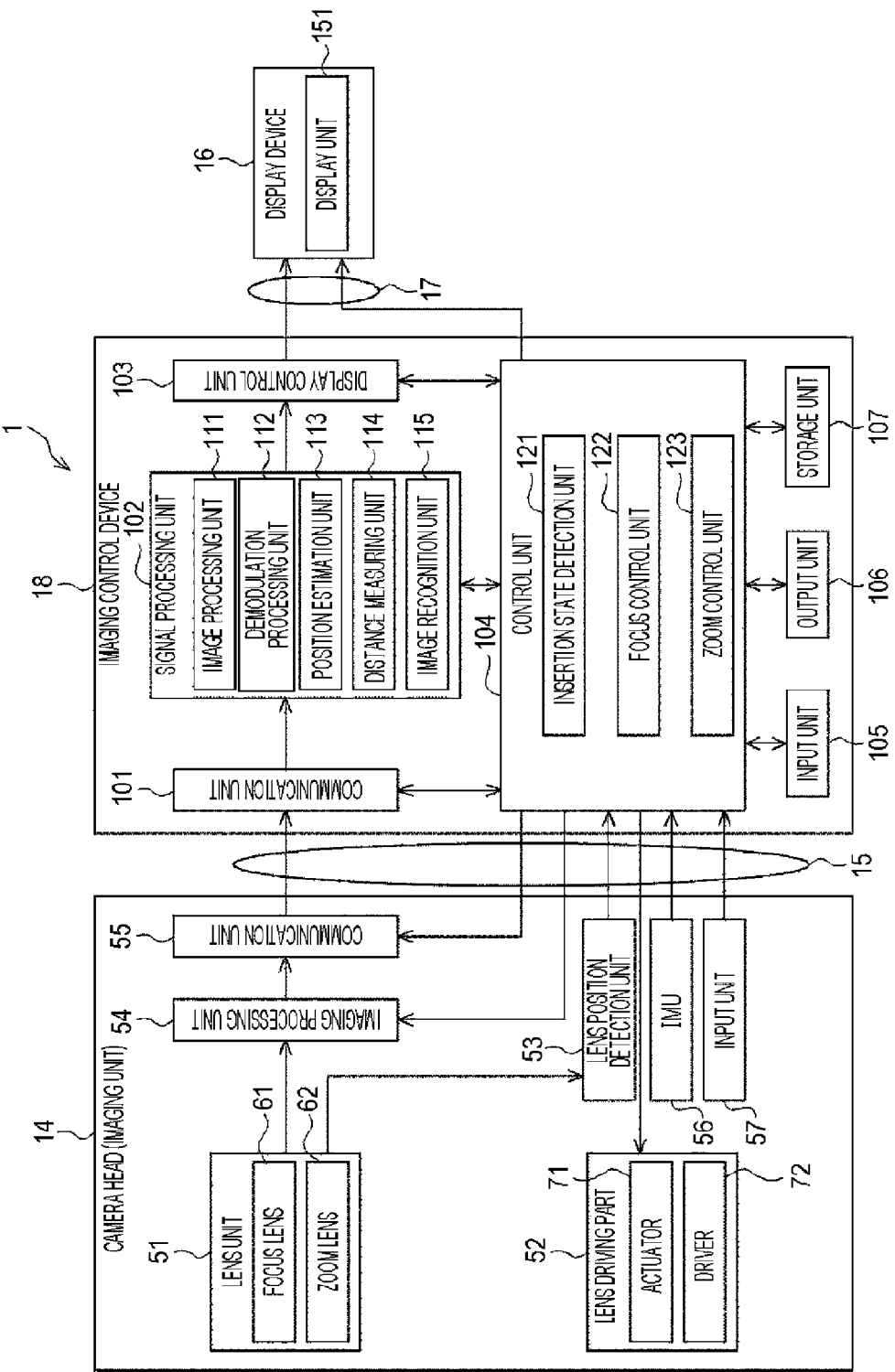
FIG. 2 is a block diagram illustrating a configuration example of a camera head, a display device, and an imaging control device.

Note that, for convenience of explanation, FIG. 2 omits illustration of the connector 20 and the connector 21 connecting each of the imaging control device 18 and the camera head 14 with the first transmission cable 15, as well as a connector connecting each of the imaging control device 18 and the display device 16 with the second transmission cable 17.

The camera head 14 includes a lens unit 51, a lens driving part 52, a lens position detection unit 53, an imaging processing unit 54, a communication unit 55, an inertial measurement unit (IMU) 56, and an input unit 57.

The lens unit 51 includes a plurality of lenses movable along the optical axis, and forms a subject image converged by the insertion part 11 onto an imaging surface of the imaging processing unit 54. The lens unit 51 includes a focus lens 61 and a zoom lens 62.

The focus lens 61 includes one or more lenses, and moves along the optical axis to adjust the focus of the camera head 14.

The zoom lens 62 includes one or more lenses, and moves along the optical axis to adjust the angle of view of the camera head 14.

Furthermore, the lens unit 51 further includes a focusing mechanism (not illustrated) for moving the focus lens 61 along the optical axis and an optical zooming mechanism (not illustrated) for moving the zoom lens 62 along the optical axis.

The lens driving part 52 includes: an actuator 71 that operates the focusing mechanism and the optical zoom mechanism described above; and a driver 72 that drives the actuator 71. In addition, the lens driving part 52 adjusts the focus and the angle of view of the lens unit 51 under the control of the imaging control device 18.

The lens position detection unit 53 is configured using a position sensor such as a photo interrupter, and detects the position of the focus lens 61 (hereinafter referred to as a focus position) and the position of the zoom lens 62 (hereinafter referred to as a zoom position). Subsequently, the lens position detection unit 53 outputs a detection signal corresponding to the focus position and the zoom position to the imaging control device 18 via the first transmission cable 15.

The imaging processing unit 54 includes a sensor chip on which an imaging element (not illustrated), a signal processing unit (not illustrated), or the like are integrated. The imaging element may include, e.g., a charge coupled device (CCD), a complementary metal oxide semiconductor (CMOS), or the like, that receives a subject image formed by the insertion part 11 and captured by the lens unit 51, and converts the image into an electrical signal. The signal processing unit performs signal processing (such as A/D conversion) on the electrical signal (analog signal) from the imaging element and outputs an image signal. Under the control of the imaging control device 18, the imaging processing unit 54 captures images of the inside the living body, and outputs an image signal (digital signal) generated by A/D conversion.

Note that the above-described signal processing unit may be separate from the imaging element, instead of being integrally formed.

The communication unit 55 functions as a transmitter that transmits the image signal output from the imaging processing unit 54 to the imaging control device 18 via the first transmission cable 15. For example, the communication unit 55 includes a high-speed serial interface for communication of an image signal with the imaging control device 18 at a transmission rate of 1 Gbps or more via the first transmission cable 15.

The IMU 56 detects the acceleration and angular velocity of the camera head 14, and supplies a detection signal indicating the detection result to the imaging control device 18.

The input unit 57 includes input devices, e.g., a button, a switch, a touch panel, or the like, and detects a user's input. The input unit 57 supplies an input signal in accordance with the user's input to the imaging control device 18.

The imaging control device 18 includes a communication unit 101, a signal processing unit 102, a display control unit 103, a control unit 104, an input unit 105, an output unit 106, and a storage unit 107.

The communication unit 101 functions as a receiver that receives an image signal output from the camera head 14 (communication unit 55) via the first transmission cable 15. For example, the communication unit 101 includes a high-speed serial interface for communication of an image signal with the communication unit 55 at a transmission rate of 1 Gbps or more.

Under the control of the control unit 104, the signal processing unit 102 performs various types of processing on the image signal (RAW signal) output from the camera head 14 (communication unit 55) and received by the communication unit 101. The signal processing unit 102 includes an image processing unit 111, a demodulation processing unit 112, a position estimation unit 113, a distance measuring unit 114, and an image recognition unit 115.

The image processing unit 111 performs RAW processing, e.g., optical black subtraction processing, demosaicing processing, or the like, on the image signal (RAW signal) received by the communication unit 101, and converts the processed RAW signal (image signal) into an RGB signal (image signal). Furthermore, the image processing unit 111 performs RGB processing, e.g., white balance, RGB gamma correction, YC conversion (converting the RGB signal into a luminance signal and a color difference signal (Y, Cb/Cr signal), etc.) or the like, on the RGB signal (image signal). Moreover, the image processing unit 111 executes YC processing, e.g., color difference correction and noise reduction on the Y and Cb/Cr signals (image signals), or the like. The image processing unit 111 supplies the image signal generated by image processing to the display control unit 103 and the control unit 104.

The demodulation processing unit 112 executes demodulation processing for controlling the camera head 14 (e.g., auto focus (AF) processing) on the image signal (e.g., Y, Cb/Cr signal) processed by the image processing unit 111. Note that the image signal is not limited to the Y, or Cb/Cr signals, and may be any signal to which image processing can be applied, and may be a RAW signal in a case where the signal has not undergone RAW processing. Furthermore, the image signal may be the luminance signal when a luminance signal (Y) is to be generated in the RAW processing.

For example, the demodulation processing unit 112 detects the contrast and frequency components of an image within a designated region on the basis of pixel information (a luminance signal (Y signal)) for each of pixels of the designated region in the captured image of one frame captured by the imaging processing unit 54. Subsequently, the demodulation processing unit 112 calculates a focus evaluation value for evaluating the focus state of the captured image (subject image in the captured image) on the basis of the detected contrast and frequency component. For example, the demodulation processing unit 112 calculates the contrast of the image in the designated region or the sum of the high frequency components of the image within the designated region, as the focus evaluation value. Note that the larger the focus evaluation value, the better the image is in focus. The demodulation processing unit 112 supplies demodulation information indicating the calculated focus evaluation value to the control unit 104.

The position estimation unit 113 performs estimation processing of the position of the camera head 14 on the basis of the image signal and the detection signal from the IMU 56. For example, on the basis of an image signal, the position estimation unit 113 creates an environmental map (three-dimensional coordinate map) and estimates the position of the camera head 14 in the environmental map using visual simultaneous localization and mapping (Visual-SLAM). Alternatively, for example, on the basis of the image signal and the detection signal from the IMU 56, the position estimation unit 113 creates an environmental map and estimates the position of the camera head 14 in the environmental map using IMU-SLAM. The position estimation unit 113 supplies position information indicating the estimation result of the position of the camera head 14 to the control unit 104.

Note that details of Visual-SLAM is described in 'Andrew J. Davison, "Real-time Simultaneous Localization and Mapping with a Single Camera", Proceedings of the 9th IEEE International Conference on Computer Vision Volume 2, 2003, pp. 1403-1410' or in JP 2011-95797 A, for example. Furthermore, the details of IMU-SLAM are described in JP 2017-185254 A, for example.

The distance measuring unit 114 measures the distance to the subject of the camera head 14, and supplies distance information indicating the measurement result to the control unit 104.

Note that a subject to be the distance measurement target may be, e.g., an organ or a part of an organ in a living body.

Furthermore, any method can be used as the measuring method of distance. For example, the imaging processing unit 54 includes an imaging element including phase difference pixels or includes a time of flight (ToF) sensor, and the distance to the subject is measured using the imaging element or the ToF sensor.

The image recognition unit 115 performs recognition processing of an object in a captured image based on an image signal. For example, the image recognition unit 115 performs recognition processing of a predetermined object such as blood, water droplets, or dirt in a captured image. Furthermore, for example, the image recognition unit 115 performs recognition processing of a surgery scene in a surgery flow using a surgical procedure or the like on the basis of a recognition result of an object in a captured image. The image recognition unit 115 supplies the control unit 104 with recognition information indicating the recognition result of the object or the recognition result of the surgery scene.

Under the control of the control unit 104, the display control unit 103 uses on-screen display (OSD) processing or the like and generates a video signal for display on the basis of the image signal (Y, Cb/Cr signal) processed by the image processing unit 111. Subsequently, the display control unit 103 outputs the generated video signal to the display device 16 (display unit 151) via the second transmission cable 17.

The control unit 104 includes a CPU or the like, and outputs a control signal via the first transmission cable 15, the second transmission cable 17, and the third transmission cable 19, thereby controlling operation of the light source device 12, the camera head 14, and the display device 16 as well as controlling the overall operation of the imaging control device 18. The control unit 104 includes an insertion state detection unit 121, a focus control unit 122, and a zoom control unit 123.

The insertion state detection unit 121 detects insertion and removal of the insertion part 11 into or from the insertion port to the living body on the basis of at least one of a detection signal from IMU 56, an image signal from image processing unit 111, demodulation information from the demodulation processing unit 112, position information from the position estimation unit 113, or distance information from the distance measuring unit 114. In other words, the insertion state detection unit 121 monitors a characteristic of the endoscope including the camera head 14 and the insertion part 11 coupled to the camera head 14, wherein the characteristic is indicative of whether the insertion part 11 is inserted in a living body or not. The characteristic may be monitored, e.g., by analyzing one or more of an image captured by an image sensor via the scope, a position of an insertion tube, an inclination of a camera head, a shape of a distal end port in an image captured by an image sensor via the scope, setting information from a support arm, or the like. Analyzing the image captured by the image sensor may include, e.g., a color of the image, a color of a peripheral portion of the image, luminance of the image, luminance of a peripheral portion of the image, or the like.

The focus control unit 122 operates the lens driving part 52 to adjust the focus of the lens unit 51 (change the focus position). For example, the focus control unit 122 executes auto focus (AF) processing on the basis of the focus position detected by the lens position detection unit 53 and the demodulation information from the demodulation processing unit 112. Furthermore, the focus control unit 122 controls AF operation on the basis of at least one of operation information from the input unit 57 or the input unit 105, the detection result of insertion and removal of the insertion part 11 obtained by the insertion state detection unit 121, or the recognition information from the image recognition unit 115. For example, the focus control unit 122 changes the condition of the focus control to control focus control operation.

Note that a continuous AF and a single-touch AF are installed as an AF function of the imaging system 1, for example. The continuous AF is basically a function to constantly (continuously) perform AF. The continuous AF is switched on or off, for example, in accordance with operation onto an operation unit (not illustrated) provided in the input unit 57 or the input unit 105. Single-touch AF is a function of performing spot AF in response to operation onto the operation unit (not illustrated) provided in the input unit 57 of the camera head 14, for example.

The zoom control unit 123 operates the lens driving part 52 to adjust the angle of view of the lens unit 51 (change the zoom position).

The input unit 105 includes input devices, e.g., a button, a switch, a mouse, a keyboard, a touch panel, or the like, and receives a user's input. The input unit 105 supplies an input signal in accordance with the user's input to the control unit 104.

The output unit 106 includes, e.g., a speaker, a printer, or the like, and outputs various types of information.

The storage unit 107 stores a program to be executed by the control unit 104, information used for processing of the control unit 104, or the like. The storage unit 107 is a non-transitory computer readable medium having stored thereon a program that, when executed by a computer, causes the control unit 104 to execute processing.

The display device 16 includes the display unit 151.

The display unit 151 includes a display panel, e.g., liquid crystal panel, an organic electro luminescence (EL) panel, or the like, and displays a display image based on a video signal from the imaging control device 18.

<Method for Inserting Insertion Part 11>

Figure 3:
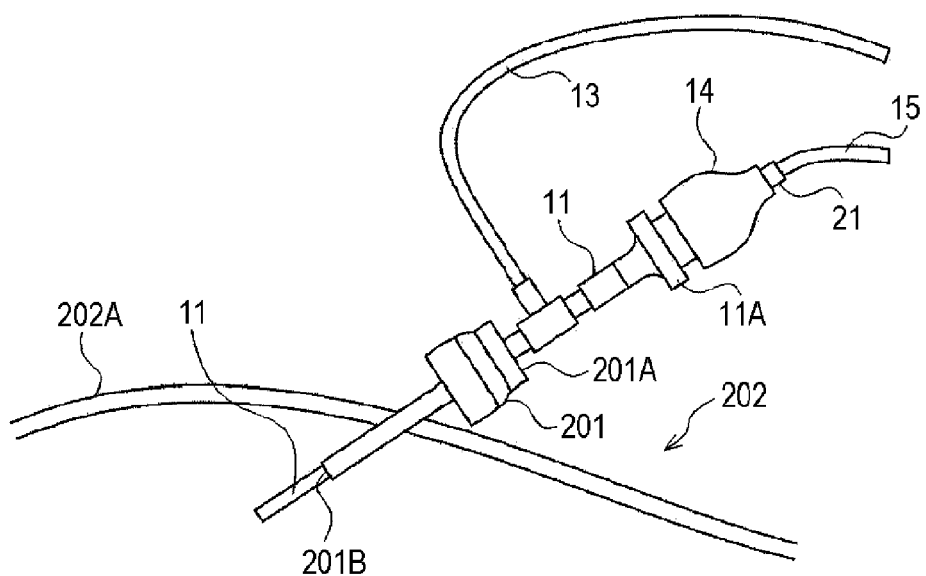
FIG. 3 is a view illustrating an example of a method for inserting an insertion part to a living body.

FIG. 3 illustrates an example of a method for inserting the insertion part 11 of the imaging system 1 into a living body 202. In this example, the insertion part 11 is inserted into the living body 202 using a trocar 201.

Specifically, the trocar 201 is inserted into skin 202A of the living body 202. Subsequently, the insertion part 11 is inserted from an insertion port 201A of the trocar 201, with a distal end of the insertion part 11 protruding from a distal end port 201B of the trocar 201. With this configuration, the insertion part 11 is inserted into the living body 202, and the position of the insertion part 11 is stabilized.

<AF Control Processing>

Figure 4:
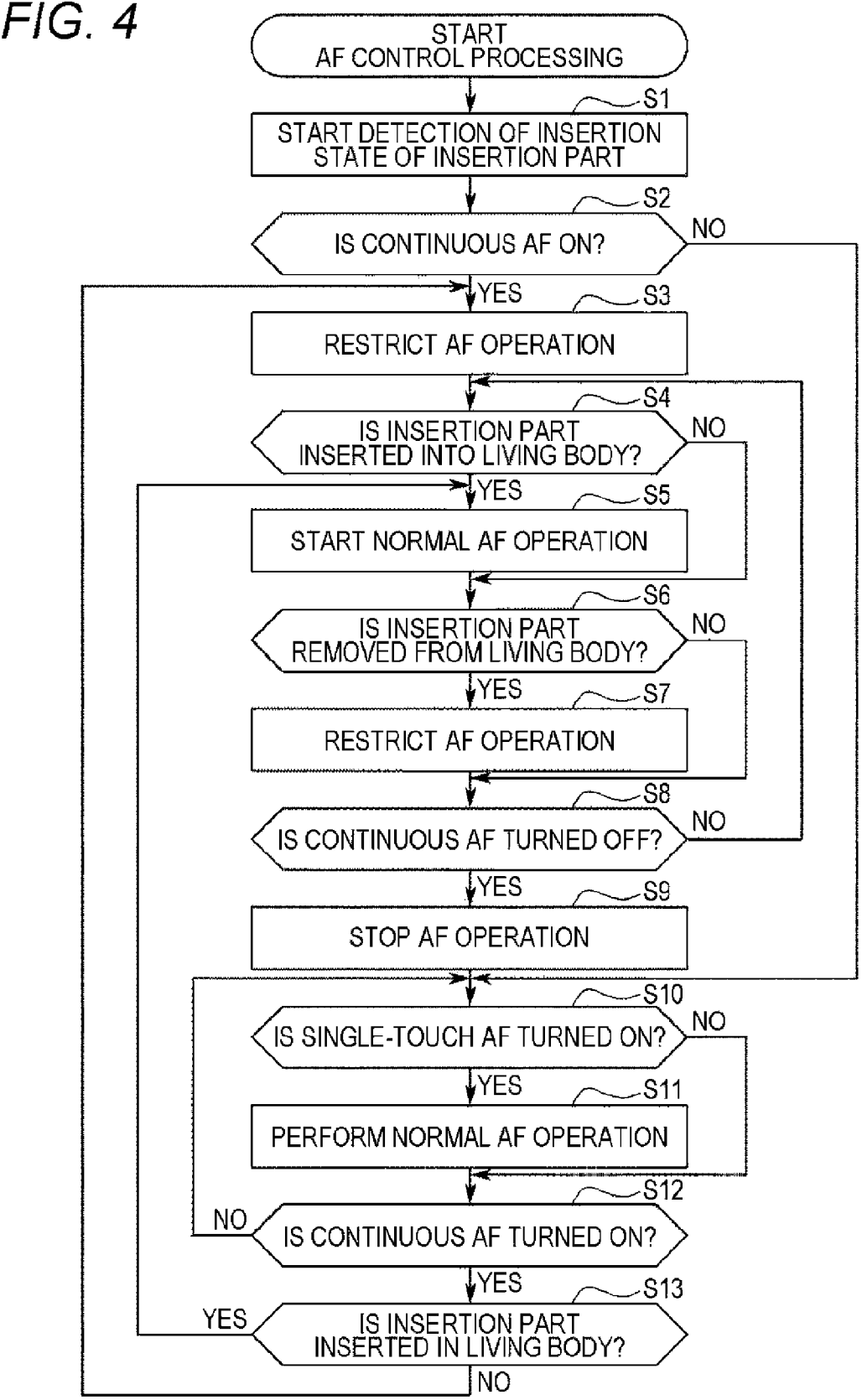
FIG. 4 is a flowchart illustrating AF control processing.

Next, AF control processing executed by the imaging system 1 will be described with reference to a flowchart in FIG. 4.

This processing is started when the power supply for the imaging control device 18 is turned on and is finished when the power supply for the imaging control device 18 is turned off, for example.

In step S1, the insertion state detection unit 121 starts detection of the insertion state of the insertion part 11. For example, the insertion state detection unit 121 starts detection of insertion and removal of the insertion part 11 into or from inside the living body.

Here, inserting the insertion part 11 into a living body represents, for example, inserting the distal end of the insertion part 11 in the direction of the living body by a predetermined distance of 0 mm or more from a predetermined insertion port. In contrast, removing the insertion part 11 from the inside of a living body represents, for example, taking out the distal end of the insertion part 11 in the direction from inside the living body by a predetermined distance of 0 mm or more from a predetermined insertion port.

Furthermore, the insertion port is an opening for inserting the insertion part 11 into the living body, and corresponds to, for example, an opening of an insertion aid (for example, the insertion port 201A of the trocar 201), a body hole, e.g., an ear hole, a nostril, an opening in an incision on the patient's body, or the like.

Furthermore, in a case where the insertion part 11 is inserted into a living body via a long tubular member such as the trocar 201, the insertion port used for detecting the insertion of the insertion part 11 may be provided separately from the insertion port used for detecting the removal of the insertion part 11. For example, the distal end port 201B of the trocar 201 of FIG. 3 may be used for detecting the insertion of the insertion part 11, and the insertion port 201A of the trocar 201 may be used for detecting the removal of the insertion part 11.

Here, an example of a method of detecting insertion of the insertion part 11 into the living body and removal of the insertion part 11 from inside the living body will be described.

For example, the insertion state detection unit 121 detects insertion and removal of the insertion part 11 on the basis of color information (or wavelength information) of a captured image.

FIGS. 5 to 8 schematically illustrate an example of captured images 251 to 254 in which the insertion part 11 is shifted from the state of being inserted in the living body using the trocar 201 to the state of being removed from inside the living body.

Figure 5:
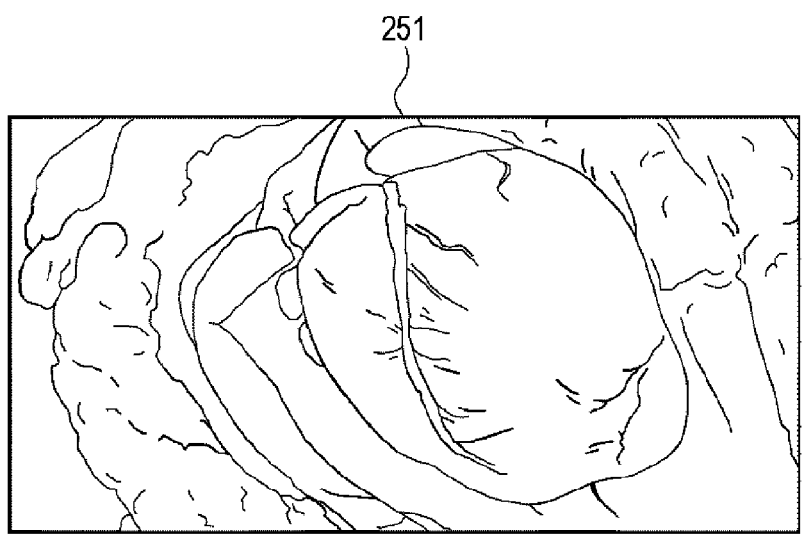
FIG. 5 is a view illustrating an example of a captured image.

Specifically, FIG. 5 is an example of a captured image 251 obtained in a state where the insertion part 11 is inserted into a living body. Since most of the captured image 251 is occupied by internal organs, most of the captured image 251 is reddish.

Figure 6:
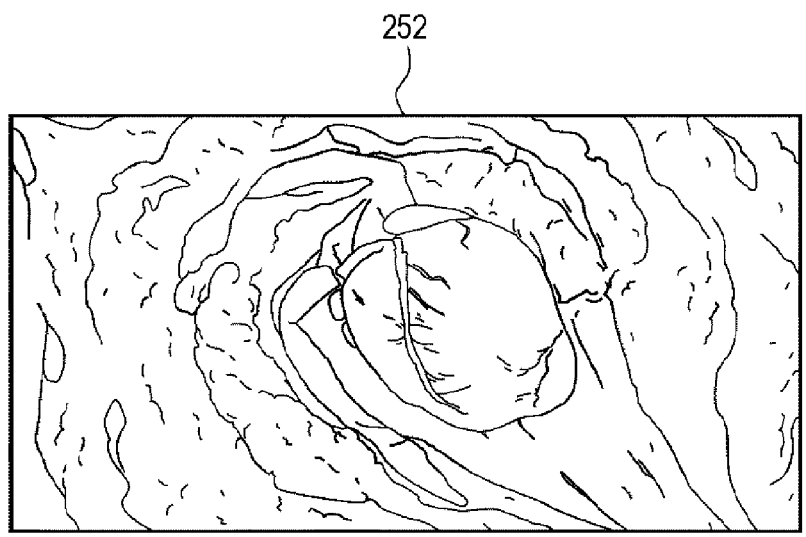
FIG. 6 is a view illustrating an example of a captured image.

FIG. 6 is an example of a captured image 252 captured, in order to remove the insertion part 11, in a state where the distal end of the insertion part 11 is slightly separated from the internal organs compared with the time of capturing the captured image 251. Since most of the captured image 252 is occupied by the internal organs, most of the captured image 252 is reddish.

Figure 7:
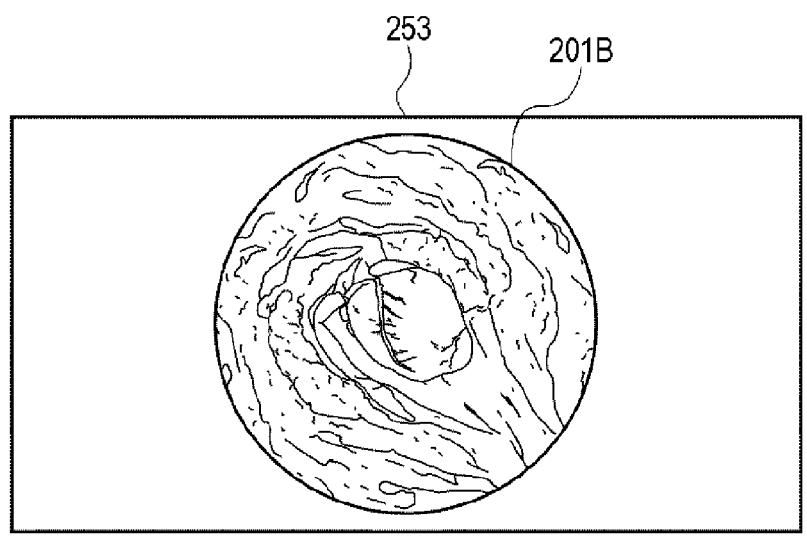
FIG. 7 is a view illustrating an example of a captured image.

FIG. 7 is an example of a captured image 253 in a state where the distal end of the insertion part 11 enters the inside of the trocar 201 slightly from the distal end port 201B of the trocar 201. Since most of the central portion of the captured image 253 viewed from the distal end port 201B is occupied by internal organs, most of the central portion of the captured image 253 is reddish. In contrast, most of the peripheral portion of the captured image is occupied by the inner wall of the trocar 201, and the light emitted from the distal end of the insertion part 11 is reflected by the inner wall. Accordingly, most of the peripheral portion of the captured image 253 is whitish (or silvery of the inner wall of the trocar). Furthermore, the peripheral portion of the captured image 253 is likely to be overexposed.

Figure 8:
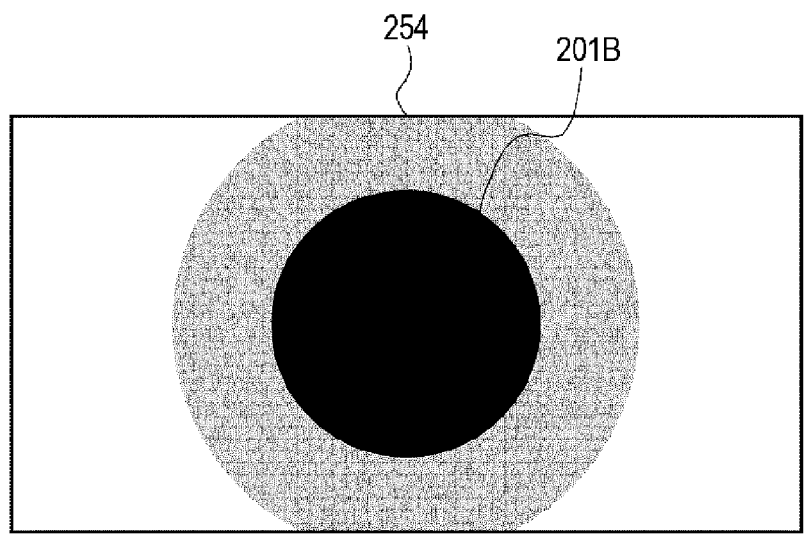
FIG. 8 is a view illustrating an example of a captured image.

FIG. 8 is an example of a captured image 254 in a state where the distal end of the insertion part 11 has been removed up to the neighborhood of the insertion port 201A of the trocar 201. In the captured image 254, the distal end port 201B in the central portion is smaller than in the captured image 253. Furthermore, since the internal organs are hardly visible from the distal end port 201B, the central portion of the captured image 254 is dark and blackish. In contrast, most of the peripheral portion of the captured image 254 is occupied by the inner wall of the trocar 201, and the light emitted from the distal end of the insertion part 11 is reflected by the inner wall. Accordingly, most of peripheral portion of the captured image 254 is whitish (or silvery of the inner wall of the trocar). Furthermore, the peripheral portion of the captured image 254 is likely to be overexposed. However, since the amount of light reflected by the inner wall is reduced in the periphery of the distal end port 201B, the color becomes darker than in the captured image 253.

The insertion state detection unit 121 detects the insertion and the removal of the insertion part 11 by using an occurrence of a great change in the color of the captured image due to the insertion and the removal of the insertion part 11 in this manner. For example, the insertion and removal of the insertion part 11 are detected on the basis of the change in the colors of the central portion and the peripheral portion of the captured image.

Specifically, for example, the insertion state detection unit 121 detects the insertion and removal of the insertion part 11 on the basis of the change in the color of the central portion when the peripheral portion of the captured image turns whitish. For example, the insertion state detection unit 121 determines that the insertion part 11 is removed in a case where the central portion of the captured image changes from reddish to blackish. In contrast, for example, the insertion state detection unit 121 determines that the insertion part 11 is inserted in a case where the central portion of the captured image changes from blackish to reddish.

Note that the insertion state detection unit 121 may detect insertion and removal of the insertion part 11 on the basis of the change in color of the peripheral portion of the captured image alone. For example, the insertion state detection unit 121 determines that the insertion part 11 is removed in a case where the peripheral portion of the captured image changes from reddish to whitish. In contrast, the insertion state detection unit 121 determines that the insertion part 11 is inserted in a case where the peripheral portion of the captured image changes from whitish to reddish. This makes it possible to reduce the amount of computation for detecting the insertion state of the insertion part 11.

Furthermore, for example, the insertion state detection unit 121 detects the insertion and removal of the insertion part 11 on the basis of the luminance of the captured image.

Specifically, in a case where the insertion part 11 is inserted into the living body, the luminance of the captured image is stable with substantially no change because there is no influence of the external light. In contrast, in a case where the insertion part 11 is removed from inside the living body, the luminance of the captured image fluctuates and becomes unstable due to the influence of the movement of the insertion part 11 or the external light. Furthermore, in a case where the distal end of the insertion part 11 is located inside the trocar 201, the light emitted from the distal end of the insertion part 11 is reflected to the inner wall of the trocar 201 to cause overexposure of the peripheral portion of the captured image, leading to a great change in the luminance.

Therefore, the insertion state detection unit 121 detects the insertion and removal of the insertion part 11 on the basis of the change in the luminance of the peripheral portion of the captured image. For example, the insertion state detection unit 121 determines that the insertion part 11 is removed in a case where the luminance of the peripheral portion of the captured image greatly changes from the stable state. In contrast, for example, the insertion state detection unit 121 determines that the insertion part 11 is inserted in a case where the luminance of the peripheral portion of the captured image greatly changes from the unstable state.

Note that the state in which the luminance of the peripheral portion of the captured image is stable represents, for example, a state in which the fluctuation range of the average value of the luminance of the peripheral portion of the captured image within a preceding predetermined period of time is less than a predetermined threshold. The state in which the luminance of the peripheral portion of the captured image is unstable represents, for example, a state in which the fluctuation range of the average value of the luminance of the peripheral portion of the captured image within a preceding predetermined period of time is a predetermined threshold or more. A great change in the luminance of the peripheral portion of the captured image represents, for example, a change in the average value of the luminance of the peripheral portion of the captured image by a predetermined threshold or more.

Alternatively, the insertion and removal of the insertion part 11 may be detected on the basis of a change in the luminance of the entire captured image, or in the luminance of a portion other than the peripheral portion of the captured image, or in the luminance of the peripheral portion and other portions of the captured image.

Furthermore, for example, the insertion state detection unit 121 detects the insertion and removal of the insertion part 11 on the basis of the position of the camera head 14 in the environmental map estimated by the position estimation unit 113. For example, the insertion state detection unit 121 detects the insertion and removal of the insertion part 11 by tracking the movement (positional change) of the camera head 14 with respect to the position of the insertion port to the living body in the environmental map.

Note that, for example, the position estimation unit 113 may estimate the position of the distal end of the insertion part 11 rather than the position of the camera head 14, and the insertion state detection unit 121 may track the movement (positional change) of the distal end of the insertion part 11 with respect to the position of the insertion port into the living body in the environmental map, thereby detecting insertion and removal of the insertion part 11.

Furthermore, for example, the insertion state detection unit 121 detects the insertion and removal of the insertion part 11 on the basis of acceleration of the camera head 14 detected by the IMU 56. For example, in a case where the change in the acceleration of the camera head 14 satisfies a predetermined condition, the insertion state detection unit 121 determines that the insertion part 11 is inserted or removed. For example, in a case where there is a change from a state in which the acceleration of the camera head 14 is substantially zero (state in which the camera head 14 is substantially stationary) to a state in which the acceleration of the camera head 14 is a predetermined threshold or more, the insertion state detection unit 121 determines that the insertion part 11 is removed. In contrast, for example, in a case where the acceleration of the camera head 14 changes from a state in which the acceleration of the camera head 14 is a predetermined threshold or more to a state in which the acceleration of the camera head 14 is substantially 0 (camera head 14 is substantially stationary), for example, the insertion state detection unit 121 determines that the insertion part 11 is inserted.

Furthermore, for example, the insertion state detection unit 121 detects the insertion and removal of the insertion part 11 on the basis of the inclination of the camera head 14 detected by the IMU 56. For example, in a case where the change in the inclination of the camera head 14 satisfies a predetermined condition, the insertion state detection unit 121 determines that the insertion part 11 is inserted or removed. For example, in a case where the inclination of the camera head 14 changes from the state in which the change in the inclination of the camera head 14 is substantially zero (state in which the camera head 14 is substantially stationary) by a predetermined threshold or more, the insertion state detection unit 121 determines that the insertion part 11 is removed. In contrast, for example, in a case where the inclination of the camera head 14 changes by a predetermined threshold or more and thereafter the change of the inclination of the camera head 14 becomes substantially zero, the insertion state detection unit 121 determines that the insertion part 11 is inserted.

Note that, for example, the IMU may be provided at the distal end of the insertion part 11, and the insertion and removal of the insertion part 11 may be detected on the basis of the acceleration or inclination of the distal end of the insertion part 11 under the similar conditions to the case of the camera head 14.

Furthermore, as illustrated in FIG. 7 and FIG. 8 described above, the distal end port 201B of the trocar 201 has a substantially circular shape in the captured image. Accordingly, for example, the image recognition unit 115 recognizes the distal end port 201B of the trocar 201 in the captured image, and the insertion state detection unit 121 detects insertion or removal of the insertion part 11 on the basis of the shape of the distal end port 201B in the captured image. For example, the insertion state detection unit 121 determines that the insertion part 11 is removed in a case where the distal end 201B is gradually reduced in size and then disappears in the captured image. The insertion state detection unit 121 determines that the insertion part 11 is inserted in a case where the distal end port 201B is gradually increased in size and then disappears in the captured image.

Furthermore, for example, the insertion state detection unit 121 detects the insertion and removal of the insertion part 11 on the basis of a focus evaluation value calculated by the demodulation processing unit 112.

Specifically, in a case where the insertion part 11 is inserted into the living body, the distance to the subject (for example, to internal organs) hardly changes, and thus, the focus evaluation value is stable with substantially no change. In contrast, in a case where the insertion part 11 is removed from inside the living body, the movement of the insertion part 11 or the subject causes the distance to the subject to fluctuate, leading to an unstable focus evaluation value with fluctuation. Furthermore, in a case where the distal end of the insertion part 11 is moving inside the trocar 201, the distance to the subject changes due to the movement of the insertion part 11, leading to a great change in the focus evaluation value.

In view of this, the insertion state detection unit 121 detects the insertion and removal of the insertion part 11 on the basis of the change in the focus evaluation value. For example, in a case where the focus evaluation value greatly changes from a stable state, the insertion state detection unit 121 determines that the insertion part 11 is removed. For example, in a case where the focus evaluation value greatly changes from an unstable state, the insertion state detection unit 121 determines that the insertion part 11 is inserted.

Note that the state in which the focus evaluation value is stable represents, for example, a state in which the fluctuation range of the focus evaluation value within a preceding predetermined period of time is less than a predetermined threshold. The state in which the focus evaluation value is unstable represents, for example, a state in which the fluctuation range of the focus evaluation value within a preceding predetermined period of time is a predetermined threshold or more. A great change in the focus evaluation value represents, for example, a change in the focus evaluation value by a predetermined threshold or more.

Note that a plurality of frames (hereinafter referred to as AF frames) may be provided in a captured image, and insertion and removal of the insertion part 11 may be detected on the basis of the focus evaluation value detected in each of the AF frames.

Figure 9:
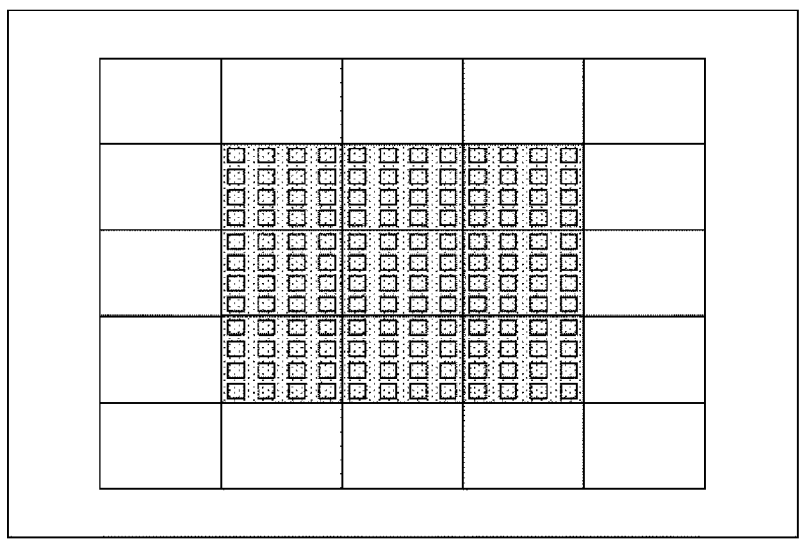
FIG. 9 is a view illustrating an example of an AF frame.

FIG. 9 illustrates an example of AF frame setting. In this example, a total of 25 large AF frames of 5 rows×5 columns are provided in the captured image. Furthermore, a total of 16 small AF frames of 4 rows×4 columns are provided within the nine AF frames in the central portion of the captured image. Accordingly, in this example, there are provided a total of 169 AF frames including 25 large AF frames and 144 small AF frames. Note that, for example, the large AF frames may be used to calculate an AF evaluation value by image contrast, and the small AF frames may be used to calculate the AF evaluation value using phase difference information in the image plane phase difference.

Subsequently, for example, the insertion state detection unit 121 detects the insertion and removal of the insertion part 11 on the basis of the change in the focus evaluation value for the peripheral portion with respect to the focus evaluation value for the AF frame of the central portion of the captured image.

Note that the insertion state detection unit 121 may detect insertion and removal of the insertion part 11 only on the basis of the change in the focus evaluation value at the central portion of the captured image or only on the basis of the change in the focus evaluation value at the peripheral portion of the captured image.

Furthermore, for example, the insertion state detection unit 121 detects the insertion and removal of the insertion part 11 on the basis of the distance to the subject measured by the distance measuring unit 114. For example, in a case where the distance to the subject greatly changes from a stable state, the insertion state detection unit 121 determines that the insertion part 11 is removed. In contrast, for example, in a case where the distance to the subject greatly changes from the unstable state, the insertion state detection unit 121 determines that the insertion part 11 is inserted.

Note that the state in which the distance to the subject is stable represents, for example, a state in which the fluctuation range of the distance within a preceding predetermined period of time is less than a predetermined threshold. The state in which the distance to the subject is unstable represents, for example, a state in which the fluctuation range of the distance within a preceding predetermined period of time is a predetermined threshold or more. A great change in the distance to the subject represents, for example, a change in the distance by a predetermined threshold or more.

Note that the detection method of insertion and removal of the insertion part 11 described above is an example, and other detection methods may be used. Furthermore, a plurality of detection methods may be combined with each other.

Referring back to FIG. 4, in step S2, the focus control unit 122 determines whether or not the continuous AF is on. In a case where it is determined that the continuous AF is on, that is, if the function of the continuous AF is enabled, the processing proceeds to step S3.

In step S3, the focus control unit 122 restricts the AF operation. For example, the focus control unit 122 stops the AF operation until the insertion part 11 is inserted into the living body. With this configuration, for example, even when the continuous AF is on in a case where the power supply of the imaging control device 18 is turned on, the AF is suppressed until the insertion part 11 is inserted into the living body.

Note that, when continuous AF is set in a case where the power supply of the imaging control device 18 is turned on, the AF operation may be started regardless of whether or not the insertion part 11 is inserted into the living body.

In step S4, the insertion state detection unit 121 determines whether or not the insertion part 11 is inserted into the living body. In a case where it is determined that the insertion part 11 is inserted into the living body, the processing proceeds to step S5.

In step S5, the focus control unit 122 starts normal AF operation. That is, the focus control unit 122 cancels the restriction of the AF operation, and operates the lens driving part 52 on the basis of the focus position detected by the lens position detection unit 53 and the demodulation information from the demodulation processing unit 112, thereby starting processing of automatically adjusting the focus of the lens unit 51.

Note that the normal AF operation may be started after a predetermined condition is satisfied, rather than starting the normal AF operation immediately after insertion of the insertion part 11 into the living body.

For example, the focus control unit 122 starts normal AF operation after a predetermined period of time (for example, several seconds) has elapsed from the time of detection of the insertion of the insertion part 11. Note that the period of time until the normal AF operation starts may be a fixed value or a variable value. In the case of a variable value, the period of time may be set on the basis of, e.g., a user setting, a period of time that elapsed before canceling the restriction on AF operation, a preset condition, or the like.

Furthermore, for example, the focus control unit 122 starts normal AF operation, e.g., the focus of the endoscope system in controlled in a first manner, when the focus evaluation value is stabilized or the luminance (brightness) of the captured image is stabilized, after the insertion of the insertion part 11 is detected. Note that the state in which the focus evaluation value is stable and the state in which the luminance of the captured image is stable are considered to be similar to the states described above.

Furthermore, for example, the normal AF operation may be gradually started after the insertion part 11 is inserted into the living body.

For example, after the insertion of the insertion part 11 is detected, the focus control unit 122 slows down the AF operation for a predetermined period of time. Specifically, for example, after the insertion of the insertion part 11 is detected, the focus control unit 122 performs AF operation with the moving speed of the focus lens 61 (that is, operating speed of AF) restricted to a predetermined value or less for a predetermined period of time. Subsequently, after a predetermined period of time has elapsed, the focus control unit 122 cancels the restriction on the moving speed of the focus lens 61. Note that the duration for delaying the AF operation may be a fixed value or a variable value. In the case of a variable value, the duration is set on the basis of, e.g., the user setting, the period of time that elapsed before canceling the restriction on AF operation, the preset condition, or the like.

This is because in case where an endoscope operator who performs operation of the imaging system 1 such as insertion and removal of the insertion part 11 removes the insertion part 11 from inside the living body and thereafter inserts the insertion part 11 again, it may take time to confirm whether or not the captured image is the same image as the image before the removal. Therefore, even when the insertion part 11 is inserted into the living body, focusing is performed by taking some time using any of the above-described methods rather than being performed immediately.

Thereafter, the processing proceeds to step S6.

In contrast, in a case where it is not determined in step S4 that the insertion part 11 is inserted into the living body, that is, the insertion part 11 remains being inserted into the living body, or the insertion part 11 remains being removed from inside the living body, the processing of step S5 is skipped, and the processing proceeds to step S6.

In step S6, the insertion state detection unit 121 determines whether or not the insertion part 11 is removed from inside the living body. In a case where it is determined that the insertion part 11 is removed from inside the living body, the processing proceeds to step S7.

In step S7, the focus control unit 122 restricts AF operation.

For example, in a case where the AF operation is continued even after the removal of the insertion part 11 from inside the living body, the focus position would greatly change in order to focus on a certain position outside the living body. Furthermore, for example, in a case where the insertion part 11 is cleaned, the focus position would constantly change due to the adhesion of water droplets or the like. Therefore, for example, this leads to continuous movement of the focus lens 61 and generation of unnecessary motion noise or vibration, which might give concern to a doctor, a nurse, an endoscope operator, a patient, or the like. Furthermore, this might cause concern of early deterioration of the actuator 71 that drives the focus lens 61.

To overcome these concerns, for example, the focus control unit 122 stops the AF operation at the moment of removal of the insertion part 11 from inside the living body, for example, the moment the insertion part 11 goes out from the insertion port. In other words, the focus of the endoscope system is controlled in a second manner, different from the first manner, e.g. to have a fixed focus position, when the insertion part 11 is removed.

Meanwhile, in a case where the insertion part 11 is inserted into a living body, the focus is on a very close position (near side) such as an internal organ. In contrast, in a case where the insertion part 11 is removed from the inside of the living body, the focus may be on a farther position (far side) than at the time of insertion, for example, a person or device in the surgical room with high probability.

Therefore, for example, removing the insertion part 11 from inside the living body and then inserting the insertion part 11 again into the living body in a state where the focus is on the far side would increase blurring of the captured image, leading to an unstable focus evaluation value. Furthermore, there is a need to move the focus lens 61 from the far side to the near side. Therefore, it would take longer time to adjust the focus after reinsertion of the insertion part 11.

Furthermore, for example, in a case where the insertion part 11 is to be removed, cleaned and then reinserted, the endoscope operator might adjust the insertion amount of the insertion part 11 so that the focus is on the target position such as the internal organ. However, when the focus position greatly changes at the time of removal of the insertion part 11, the target position would not be in focus at the time of re-insertion, making it difficult for the endoscope operator to determine how deep the insertion part 11 should be inserted.

To handle this, for example, the focus control unit 122 fixes the focus position (position of the focus lens 61) to the position at the moment of removal of the insertion part 11 from inside the living body or at a predetermined reference position. Alternatively, for example, the focus control unit 122 restricts the focus position operation range to a range narrower than at the time before the removal of the insertion part 11 from inside the living body. In this case, the focus control unit 122 sets the focus position operation range after the restriction on the basis of the focus position at the moment of removal of the insertion part 11 from inside the living body or the reference position, for example.

The reference position is set to a position (that is, the near side) at which the subject at a predetermined short distance (for example, several millimeters to several centimeters) is in focus, for example. Specifically, for example, the reference position is set to the focus position to be used in a case where the internal organ in the living body is in focus.

Alternatively, the reference position is set to the focus position immediately before removal of the insertion part 11. For example, the focus control unit 122 constantly stores the focus position within a preceding predetermined period of time. Subsequently, in a case where removal of the insertion part 11 is detected, the focus control unit 122 sets the focus position in a stable state immediately before the removal of the insertion part 11, as the reference position. For example, the focus control unit 122 sets, as the reference position, an average value of focus positions in a period in which the focus position immediately before the removal of the insertion part 11 is stable (for example, a period in which the focus position fluctuation range is less than a predetermined threshold).

In this manner, fixing the focus position or restricting the focus position operation range would make it possible to quickly set a desired target position (for example, internal organs) in focus in a case where AF is resumed.

Thereafter, the processing proceeds to step S8.

In contrast, in a case where it is not determined in step S6 that the insertion part 11 is removed from inside the living body, that is, the insertion part 11 remains being inserted into the living body, or the insertion part 11 remains being removed from inside the living body, the processing of step S7 is skipped, and the processing proceeds to step S8.

In step S8, the focus control unit 122 determines whether or not the continuous AF is turned off on the basis of the input signal from the input unit 57 or the input unit 105. In a case where it is determined that the continuous AF is not turned off, the processing returns to step S4.

Thereafter, the processing of steps S4 to S8 is repeatedly executed until it is determined in step S8 that the continuous AF is turned off.

In contrast, in a case where it is determined in step S8 that the continuous AF is turned off, the processing proceeds to step S9. This is assumed to be a case, for example, where the user performs continuous AF turn-off operation using the input unit 57 or the input unit 105.

In step S9, the focus control unit 122 stops the AF operation.

Thereafter, the processing proceeds to step S10.

In contrast, in a case where it is determined in step S2 that the continuous AF is off, the processing of steps S3 to S9 is skipped and the processing proceeds to step S10. This corresponds to a case, for example, where the continuous AF is off in a case where the power supply of the imaging control device 18 is turned on.

In step S10, the focus control unit 122 determines whether or not single-touch AF is turned on, on the basis of the input signal from the input unit 57. In a case where it is determined that the single-touch AF is turned on, the processing proceeds to step S11. This is assumed to be a case, for example, where the user uses the input unit 57 to perform single-touch AF turn-on operation.

In step S11, the focus control unit 122 performs normal AF operation. With this configuration, a desired target position such as an internal organ comes in focus, for example.

Thereafter, the processing proceeds to step S12.

In contrast, in a case where it is determined in step S10 that the single-touch AF is not turned on, the processing in step S11 is skipped and the processing proceeds to step S12.

In step S12, the focus control unit 122 determines whether or not the continuous AF is turned on the basis of the input signal from the input unit 57 or the input unit 105. In a case where it is determined that the continuous AF is not turned on, the processing returns to step S10.

Thereafter, the processing of steps S10 to S12 is repeatedly executed until it is determined in step S12 that the continuous AF is turned on.

In contrast, in a case where it is determined in step S12 that the continuous AF is turned on, the processing proceeds to step S13. This is assumed to be a case, for example, where the user performs continuous AF turn-on operation using the input unit 57 or the input unit 105.

In step S13, the insertion state detection unit 121 determines whether or not the insertion part 11 is inserted into a living body. In a case where it is determined that the insertion part 11 is inserted into the living body, the processing returns to step S5, and the processing of step S5 and subsequent processing are executed. That is, in a case where the continuous AF is turned on in a state where the insertion part 11 is inserted into the living body, the normal AF operation is started.

In contrast, in a case where it is determined in step S13 that the insertion part 11 is not inserted into the living body, the processing returns to step S3 and the processing of step S3 and subsequent processing are executed. That is, in a case where the continuous AF is turned on in a state where the insertion part 11 is not inserted into the living body, the normal AF operation is restricted until the insertion part 11 is inserted into the living body.

As described above, the stable AF operation can be achieved in the case of imaging the inside of a living body. For example, when the insertion part 11 is removed from inside the living body and then reinserted in a case where the continuous AF is turned on, it is possible to quickly set the same subject as before the removal in focus.

2. MODIFICATIONS

Hereinafter, a modification of the above-described embodiments of the present technology will be described.
<Modification Regarding Detection Processing of Insertion State of Insertion Part 11>

Figure 10:
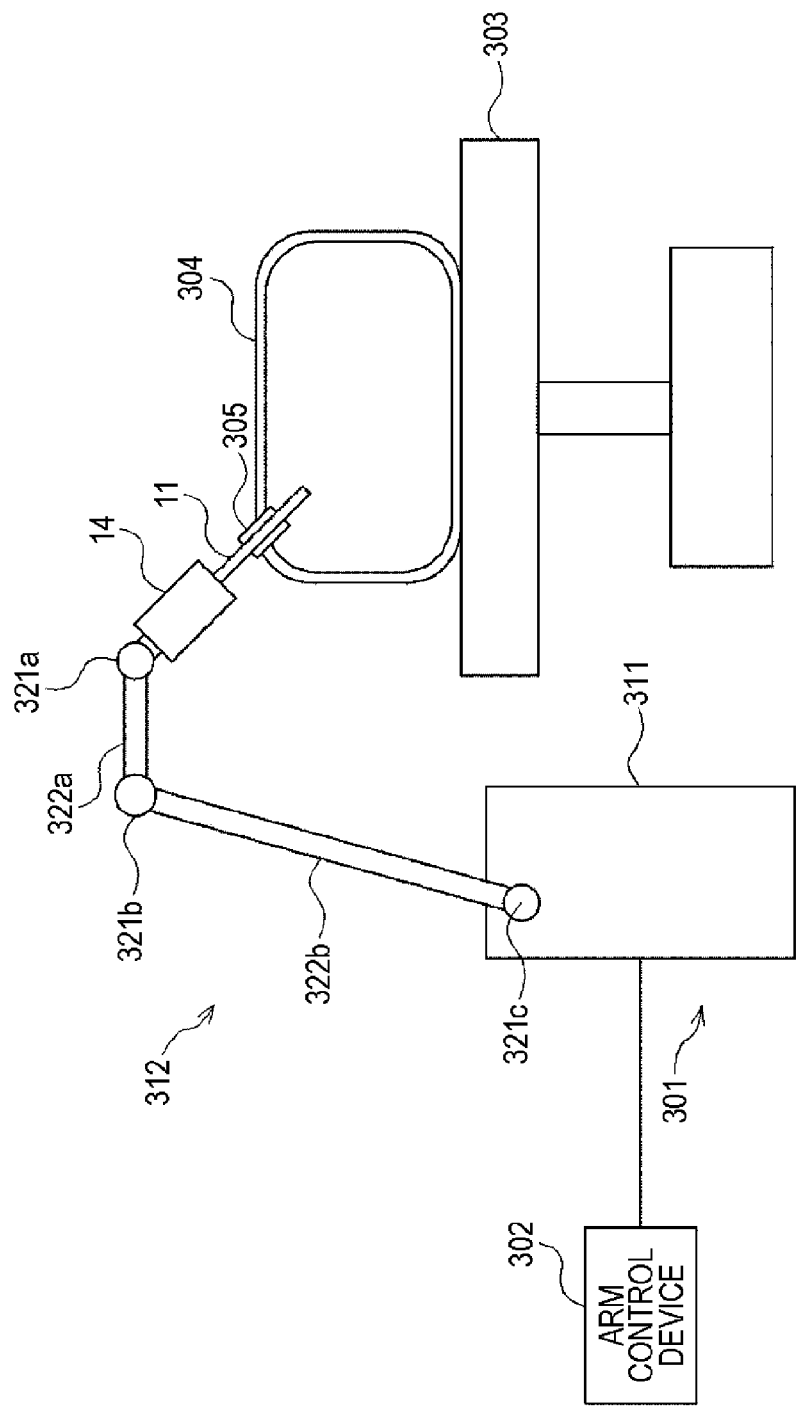
FIG. 10 is a diagram illustrating a configuration example of a support arm device.

For example, as illustrated in FIG. 10, in a case where the camera head 14 and the insertion part 11 are moved while being supported by the support arm device 301, the insertion state detection unit 121 may detect insertion and removal of the insertion part 11 on the basis of the movement of the support arm device 301.

The support arm device 301 includes a base unit 311 as a base and an arm part 312 extending from the base unit 311. In this example, the arm part 312 includes: a plurality of joints 321a to 321c; and a plurality of links 322a and links 322b connected by the joints 321b.

The arm control device 302 drives actuators provided in the joints 321a to 321c and controls the rotation angles of the joints 321a to 321c to control the movement of the arm part 312. Subsequently, the arm part 312 is driven to control the position and posture of the camera head 14 and the insertion part 11, allowing the insertion part 11 to be inserted into the body of a patient 304 on a patient bed 303 via the trocar 305 from the desired direction.

Following this, for example, the insertion state detection unit 121 estimates the position of the distal end of the insertion part 11 on the basis of information regarding the movement of the support arm device 301 (arm part 312) output from the arm control device 302, thereby detecting insertion and removal of the insertion part 11.

Furthermore, for example, in a case where an insertion mode for inserting the insertion part 11 into the living body and a removal mode for removing the insertion part 11 from inside the living body is provided in the support arm device 301 or the arm control device 302, the insertion state detection unit 121 may detect insertion and removal of the insertion part 11 on the basis of setting information output from the support arm device 301 or the arm control device 302 at the setting of the insertion mode and the removal mode.

Furthermore, as described above, the insertion and removal of the insertion part 11 may be detected by combining a plurality of detection methods (for example, a method using the luminance of the captured image and a method using the focus evaluation value). However, combining a plurality of detection methods would presumably lead to a state in which a detection result differs for each of individual detection methods. To handle this, for example, detection methods may be prioritized, e.g., based on the detection accuracy, computational efficiency, or the like. The detection result obtained by the detection method having a higher priority may be adopted.

Furthermore, a detection method with low detection accuracy and a small amount of computation (for example, a method using the luminance of a captured image) may be used constantly, while a detection method with high detection accuracy and with a large amount of computation (for example a method using image recognition) may be used temporarily. For example, in a case where removal of the insertion part 11 is detected by the detection method with a small amount of computation, detection processing using the detection method with a large amount of computation intermittently (for example, every 10 seconds) may be performed. For example, in a case where the insertion of the insertion part 11 is detected by a method with a large amount of computation, but the insertion of the insertion part 11 is not detected by a method with a small amount of computation, the detection result of the higher detection accuracy may be adopted to determine that the insertion part 11 is inserted. In this case, after the insertion of the insertion part 11 is detected, the detection processing by the detection method with a large amount of computation is to be stopped.

Furthermore, for example, in a case where the insertion of the insertion part 11 is not detected within a predetermined period of time (for example, within five minutes) after detection of the removal of the insertion part 11, the detection result may be considered erroneous such that the insertion part 11 is determined to be inserted.
<Modification Regarding AF Operation>

For example, the focus control unit 122 may control the AF operation on the basis of a surgery flow recognized by the image recognition unit 115 or the like. For example, the focus control unit 122 may control the AF operation on the basis of the presence or absence of bleeding, on-off states of the electrical knife, or the like.

Furthermore, for example, in a case where the image recognition unit 115 detects adhesion of blood, water droplets, dirt, or the like to the lens of the insertion part 11 on the basis of a captured image, the focus control unit 122 may stop the AF operation.

<Modification Regarding User Interface>

For example, setting of the continuous AF in a case where the insertion part 11 is inserted into a living body may be facilitated.

For example, in a case where single-touch AF operation is performed in a case where the insertion part 11 is inserted into the living body, the continuous AF may be automatically turned on after the single-touch AF operation is performed. Note that in this case, the period during which the continuous AF is automatically turned on by single-touch AF operation may be restricted to a predetermined period of time (for example, within several minutes) after the insertion part 11 is inserted into the living body.

Furthermore, for example, the continuous AF operation and the single-touch AF operation may be performed by the same operation device. For example, in a case where the operation button is pressed for a short time, a single-touch AF may be performed and, in a case where the operation button is pressed for a long time, the continuous AF setting is turned from on to off or off to on.

Furthermore, for example, the display unit 151 may display the operation state of the continuous AF under the control of the display control unit 103. For example, letters indicating the operation state, e.g., AF-C, of a particular color, e.g., green, may be displayed, e.g., in a corner of the captured image in a case where the normal continuous AF operation is performed. In a case where the continuous AF operation is restricted, these letters change to alert the operator that AF operation is restricted. For example, these letters may turn a different color that provides good contrast with the image, e.g., white, may increase in size, may blink, or the like. Additionally or alternatively, other types of warning, e.g., audible warnings or the like may be used.

Figure 11:
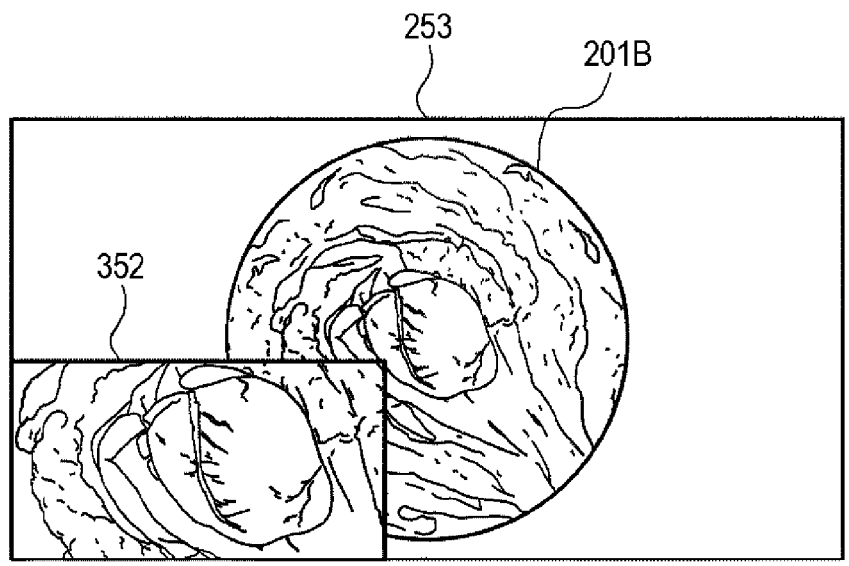
FIG. 11 is a view illustrating an example of displaying a captured image.

Furthermore, as illustrated in FIG. 11, the stably focused captured image 352 may be displayed in the form of picture in picture (PinP) on the captured image 351 displayed in real time. Note that in the example of FIG. 11, an image of the distal end port 201B of the insertion part 11 appears in the captured image 351.

For example, the captured image 352 is to be the latest (real-time) image among captured images captured in a stably focused state (for example, a state hi which the fluctuation range of the focus evaluation value within a predetermined period of time is less than a predetermined threshold). In this case, the captured image 351 and the captured image 352 may match in a case where a stably focused state is achieved at the current point in time.

Alternatively, for example, in a case where the insertion part 11 has already been removed from inside the living body, a captured image captured in a stably focused state immediately before the removal of the insertion part 11 is displayed as the captured image 352.

Note that the captured image 352 is displayed in a case where the insertion part 11 is removed from the inside of the living body and not display the captured image 352 in a case where the insertion part 11 is inserted inside the living body. Alternatively, the captured image 352 alone may be displayed in a case where the insertion part 11 is removed from the inside of a living body. In any case, for example, display of the captured image 352 is started in a case where removal of the insertion part 11 is detected, and display of the captured image 352 is stopped in a case where insertion of the insertion part 11 is detected.

<Modification Regarding Configuration Example of Imaging System>

The configuration example of the imaging system 1 described above is an example and can be modified. For example, part of the functions of the camera head 14 can be transferred to the imaging control device 18 or part of the functions of the imaging control device 18 can be transferred to the camera head 14.

For example, one or more of the insertion state detection unit 121, the focus control unit 122, and the zoom control unit 123 of the imaging control device 18 may be provided in the camera head 14. In this case, the camera head 14 controls the AF operation.

Furthermore, for example, the functions of part or entire of the image processing unit 111 and the demodulation processing unit 112 of the imaging control device 18 may be provided in the camera head 14.

3. OTHERS

<Configuration Example of Computer>

A series of processing described above can be executed by hardware or by software. In a case where the series of processing is executed by software, a program included in the software is installed in a computer. Herein, the computer includes a computer incorporated in a dedicated hardware, for example, a general-purpose personal computer on which various types of functions can be executed by installing various programs, or the like. As used herein 'computer' refers to circuitry that may be configured via the execution of computer readable instructions, and the circuitry may include one or more local processors (e.g., CPU's), and/or one or more remote processors, such as a cloud computing resource, or any combination thereof.

FIG. 12 is a block diagram illustrating an exemplary configuration of hardware of a computer in which the series of processing described above is executed by a program.

In the computer, a central processing unit (CPU) 1001, a read only memory (ROM) 1002, and a random access memory (RAM) 1003 are interconnected via a bus 1004.

The bus 1004 is further connected with an input/output interface 1005. The input/output interface 1005 is connected with an input unit 1006, an output unit 1007, a storage unit 1008, a communication unit 1009, and a drive 1010.

The input unit 1006 includes a keyboard, a mouse, a microphone, or the like. The output unit 1007 includes a display, a speaker, or the like. The storage unit 1008 includes a hard disk, a non-volatile memory, or the like. The communication unit 1009 includes a network interface or the like. The drive 1010 drives a removable medium 1011 including a magnetic disk, an optical disk, a magneto-optical disk, a semiconductor memory, or the like.

On the computer configured as above, the series of above-described processing is executed by operation such that the CPU 1001 loads, for example, a program stored in the storage unit 1008 onto the RAM 1003 via the input/output interface 1005 and the bus 1004 and executes the program.

The program executed by the computer (CPU 1001) can be stored, for example, in the removable medium 1011 as a package medium or the like and be provided. Alternatively, the program can be provided via a wired or wireless transmission medium including a local area network, the Internet, and digital satellite broadcasting.

On the computer, the program can be installed in the storage unit 1008 via the input/output interface 1005, by attaching the removable medium 1011 to the drive 1010.

Furthermore, the program can be received at the communication unit 1009 via a wired or wireless transmission medium and be installed in the storage unit 1008. Alternatively, the program can be installed in the ROM 1002 or the storage unit 1008 beforehand.

Note that the program executed by the computer may be a program processed in time series in an order described in the present description, or can be a program processed in parallel or in necessary timing such as being called.

Moreover, in the present description, the system represents a set of multiple constituents (devices, modules (components), or the like). In other words, all the constituents may be in the same housing but they do not have to be in the same housing. Accordingly, a plurality of devices, housed in separate housings, connected via a network can be a system. A device containing a plurality of modules in one housing can also be a system.

Note that embodiments of the present technology are not limited to the above-described embodiments but can be modified in a variety of ways within a scope of the present technology.

For example, the present technology can be configured as a form of cloud computing in which one function is shared in cooperation for processing among a plurality of devices via a network. Also, the present technology can be configured as a form of a server or IP converter in a hospital in which one function is shared in cooperation for processing among a plurality of devices via a network.

Moreover, each of steps described in the above flowcharts can be executed on one device or shared by a plurality of devices for processing.

Furthermore, in a case where one step includes a plurality of stages of processing, the plurality of stages of processing included in the one step can be executed on one device or shared by a plurality of devices for processing.

<Configuration Combination Example>

The present technology can also be configured as follows.

(1)

An endoscope system including:

an insertion state detection unit configured to detect an insertion state indicating whether or not an insertion part equipped with an optical system and connected with an imaging unit is inserted into a living body; and a focus control unit configured to control focus control operation of the imaging unit on the basis of a result of the detection of the insertion state.

(2)

The endoscope system according to (1), in which the focus control unit restricts the focus control operation in a case where the insertion part is removed from inside the living body.

(3)

The endoscope system according to (2), in which the focus control unit fixes a focus position of the imaging unit in a case where the insertion part is removed from inside the living body.

(4)

The endoscope system according to (2), in which, in a case where the insertion part is removed from inside the living body, the focus control unit controls operation of the focus control such that an operation range of the focus position of the imaging unit is within a predetermined range narrower than a range before the removal of the insertion part.

(5)

The endoscope system according to (2), in which the focus control unit fixes the focus position of the imaging unit at a position before the removal of the insertion part from inside the living body.

(6)

The endoscope system according to (2), in which the focus control unit controls operation of the focus control such that an operation range of the focus position of the imaging unit is within a predetermined range including a position before the removal of the insertion part from inside the living body on the basis of the position before the removal of the insertion part from inside the living body.

(7)

The endoscope system according to (2), in which the focus control unit fixes the focus position of the imaging unit at a position where a subject at a predetermined short distance is in focus or reduces the operation range of the focus position to be narrower than the operation range before the removal of the insertion part on the basis of the position where the subject is in focus.

(8)

The endoscope system according to (2), in which the focus control unit stops the focus control operation in a case where the insertion part is removed from inside the living body.

(9)

The endoscope system according to any of (2) to (8), in which the focus control unit cancels restriction of the focus control operation in a case where the insertion part is inserted into the living body.

(10)

The endoscope system according to (9), in which the focus control unit cancels restriction of the focus control operation after a predetermined period of time has elapsed from the time of insertion of the insertion part into the living body.

(11)

The endoscope system according to any of (2) to (8), in which the focus control unit cancels restriction of the focus control operation when a focus evaluation value for evaluating a focus state of a captured image obtained by the imaging unit is stabilized, or brightness of the captured image is stabilized, after the insertion of the insertion part into the living body.

(12)

The endoscope system according to any of (1) to (11), in which the focus control unit slows down an operation speed of the focus control for a predetermined period of time after the insertion of the insertion part into the living body.

(13)

The endoscope system according to any of (1) to (12), in which the insertion state detection unit detects insertion of the insertion part into an insertion port to the living body and removal of the insertion part from the insertion port.

(14)

The endoscope system according to any of (1) to (13), in which the insertion state detection unit detects insertion and removal of the insertion part on the basis of the captured image obtained by the imaging unit.

(15)

The endoscope system according to (14), in which the insertion state detection unit detects insertion and removal of the insertion part on the basis of a change in luminance of the captured image.

(16)
The endoscope system according to (15),
in which the insertion state detection unit detects insertion and removal of the insertion part on the basis of a change in luminance of a peripheral portion of the captured image.

(17)
The endoscope system according to any of (14) to (16),
in which the insertion state detection unit detects insertion and removal of the insertion part on the basis of a change in a focus evaluation value for evaluating a focus state of the captured image.

(18)
The endoscope system according to any of (14) to (17),
in which the insertion state detection unit detects insertion and removal of the insertion part on the basis of a change in colors of the captured image.

(19)
The endoscope system according to any of (13) to (18), further including
an image recognition unit that recognizes the insertion port in the image captured by the imaging unit,
in which the insertion state detection unit detects insertion and removal of the insertion part on the basis of a shape of the insertion port in the captured image.

(20)
The endoscope system according to any of (1) to (19),
in which the insertion state detection unit acquires measured distance information indicating a distance to a subject, and detects insertion and removal of the insertion part on the basis of a change in the measured distance information.

(21)
The endoscope system according to any of (1) to (20), further including
a position estimation unit configured to estimate a position of at least one of the imaging unit or the insertion part,
in which the insertion state detection unit detects insertion and removal of the insertion part on the basis of a change in the position of at least one of the imaging unit or the insertion part.

(22)
The endoscope system according to any of (1) to (21),
in which the insertion state detection unit detects insertion and removal of the insertion part on the basis of an output regarding an arm part that controls position and posture of the imaging unit.

(23)
The endoscope system according to any of (1) to (22),
in which the insertion state detection unit detects insertion and removal of the insertion part on the basis of a change in acceleration of at least one of the imaging unit or the insertion part.

(24)
The endoscope system according to any of (1) to (23),
in which the insertion state detection unit detects insertion and removal of the insertion part on the basis of a change in inclination of at least one of the imaging unit or the insertion part.

(25)
The endoscope system according to any of (1) to (24), further including
a display control unit configured to control a display unit to display a first captured image obtained by the imaging unit before the removal of the insertion part from inside the living body, in a case where the insertion part is removed from inside the living body.

(26)
The endoscope system according to (25),
in which the display control unit controls the display unit to display the first captured image together with a real-time second captured image obtained by the imaging unit.

(27)
The endoscope system according to (26),
in which the display control unit controls the display unit to stop displaying the first captured image in a case where the insertion part is inserted from inside the living body.

(28)
The endoscope system according to any of (1) to (27),
in which the focus control unit performs control so as to continuously perform the focus control when operation of the focus control is performed as spot operation in a case where the insertion part is inserted into the living body.

(29)
An endoscope control method, including:
detecting an insertion state indicating whether or not an insertion part equipped with an optical system and connected with an imaging unit is inserted into a living body; and
controlling focus control operation of the imaging unit on the basis of a result of the detection of the insertion state.

(30)
An imaging control device including:
an insertion state detection unit configured to detect an insertion state indicating whether or not an insertion part equipped with an optical system and connected with an imaging unit is inserted into a living body; and
a focus control unit configured to control focus control operation of the imaging unit on the basis of a result of the detection of the insertion state.

<Modification Regarding Configuration Combination Example>

The present technology can also be configured as follows.

(31)
An endoscope system, including:
circuitry configured to:
monitor a characteristic of an endoscope including an imaging device and a scope coupled to the imaging device, wherein the characteristic is indicative of whether the scope is inserted in a living body or not;
in the event that the characteristic satisfies a predetermined condition, control a focus of the endoscope system in a first manner; and
in the event that the characteristic does not satisfy the predetermined condition, control the focus of the endoscope system in a second manner, different from the first manner.

(32)
The endoscope system according (31), wherein the first manner includes auto focusing the focus of the endoscope system.

(33)
The endoscope system according to (31), wherein the first manner includes setting the focus of the endoscope system to a fixed focus position.

(34)
The endoscope system according to (33), wherein the fixed focus position is set to a focus position just prior to the characteristic satisfying the predetermined condition.

(35)
The endoscope system according to any of (31) to (34), wherein the characteristic is a characteristic of an image captured by an image sensor via the scope.

(36)

The endoscope system according to (35), wherein the characteristic is a color of the image.

(37)

The endoscope system according to (35), wherein the characteristic is a color of a peripheral portion of the image.

(38)

The endoscope system according to (35), wherein the characteristic is a luminance of the image.

(39)

The endoscope system according to claim (35), wherein the characteristic is a fluctuation of luminance in a peripheral portion of the image within a predetermined period of time.

(40)

The endoscope system according to any of (31) to (39), wherein the characteristic is a position of an insertion tube of the endoscope system.

(41)

The endoscope system according to any of (31) to (40), wherein the characteristic is an inclination of a camera head of the endoscope system.

(42)

The endoscope system according to any of (31) to (41), wherein the characteristic is an acceleration of a camera head of the endoscope system.

(43)

The endoscope system according to any of (31) to (42), wherein the characteristic is a shape of a distal end port in an image captured by an image sensor via the scope.

(44)

The endoscope system according to any of (31) to (43), wherein the characteristic is a focus evaluation value of the endoscope system.

(45)

The endoscope system according to any of (31) to (44), wherein the characteristic is a setting information from a support arm of the endoscope system.

(46)

The endoscope system according to any of (31) to (45), wherein the circuitry is further configured to display, in the event that the characteristic satisfies the predetermined condition, a first captured image obtained by the imaging device just prior to the characteristic satisfying the predetermined condition.

(47)

The endoscope system according to (46), wherein the circuitry is further configured to stop displaying the first captured image and display a real-time captured image in the event that the characteristic does not satisfy the predetermined condition.

(48)

The endoscope system according to any of (31) to (47), wherein, after the characteristic satisfies the predetermined condition and then stops satisfying the predetermined condition, the circuitry is to control the focus of the endoscope system in the second manner gradually.

(50)

A non-transitory computer readable medium having stored thereon a program that, when executed by a computer, causes the computer to execute processing, the processing including:

monitoring a characteristic of an insertion portion that is to be inserted in and removed from a living body, the insertion portion to be connected to an image sensor that generate an image in a medical imaging system;

in the event that the characteristic satisfies a predetermined condition, controlling a focus of the medical imaging system in a first manner; and in the event that the characteristic does not satisfy the predetermined condition, controlling the focus of the medical imaging system in a second manner, different from the first manner.

(60)

A method, including:

monitoring a characteristic of an insertion portion that is to be inserted in and removed from a living body, the insertion portion to be connected to an image sensor that generates an image in a medical imaging system;

in the event that the characteristic satisfies a predetermined condition, controlling a focus of the medical imaging system in a first manner; and in the event that the characteristic does not satisfy the predetermined condition, controlling the focus of the medical imaging system in a second manner, different from the first manner.

Note that effects described herein are provided for purposes of exemplification and are not intended to be limiting. Still other effects may also be contemplated.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Imaging system
11 Insertion part
14 Camera head
18 Imaging control device
51 Lens unit
52 Lens driving part
53 Lens position detection unit
54 Imaging processing unit
61 Focus lens
71 Actuator
102 Signal processing unit
103 Display control unit
104 Control unit
111 Image processing unit
112 Demodulation processing unit
113 Position estimation unit
114 Distance measuring unit
115 Image recognition unit
121 Insertion state detection unit
122 Focus control unit
151 Display unit
201 Trocar
201A Insertion port
201B Distal end port
301 Support arm device
302 Arm control device
312 Arm portion

The invention claimed is:

1. An endoscope system, comprising:
circuitry configured to:
monitor a characteristic of an endoscope including an imaging device and a scope coupled to the imaging device, wherein the characteristic is indicative of whether the scope is inserted in a living body or not;

in the event that the characteristic satisfies a predetermined condition, control a focus of the endoscope system in a first manner; and in the event that the characteristic does not satisfy the predetermined condition, control the focus of the endoscope system in a second manner, different from the first manner, wherein the first manner includes auto focusing the focus of the endoscope system.

2. The endoscope system according to claim 1, wherein the second manner includes setting the focus of the endoscope system to a fixed focus position.

3. The endoscope system according to claim 2, wherein the fixed focus position is set to a focus position just prior to the characteristic satisfying the predetermined condition.

4. The endoscope system according to claim 1, wherein the characteristic is a characteristic of an image captured by an image sensor via the scope.

5. The endoscope system according to claim 4, wherein the characteristic is a color of the image.

6. The endoscope system according to claim 4, wherein the characteristic is a color of a peripheral portion of the image.

7. The endoscope system according to claim 4, wherein the characteristic is a luminance of the image.

8. The endoscope system according to claim 4, wherein the characteristic is a fluctuation of luminance in a peripheral portion of the image within a predetermined period of time.

9. The endoscope system according to claim 1, wherein the characteristic is a position of an insertion tube of the endoscope system.

10. The endoscope system according to claim 1, wherein the characteristic is an inclination of a camera head of the endoscope system.

11. The endoscope system according to claim 1, wherein the characteristic is an acceleration of a camera head of the endoscope system.

12. The endoscope system according to claim 1, wherein the characteristic is a shape of a distal end port in an image captured by an image sensor via the scope.

13. The endoscope system according to claim 1, wherein the characteristic is a focus evaluation value of the endoscope system.

14. The endoscope system according to claim 1, wherein the characteristic is a setting information from a support arm of the endoscope system.

15. The endoscope system according to claim 1, wherein the circuitry is further configured to output to a display, in the event that the characteristic satisfies the predetermined condition, a first captured image obtained by the imaging device just prior to the characteristic satisfying the predetermined condition.

16. The endoscope system according to claim 15, wherein the circuitry is further configured to stop output of the first captured image and output a real-time captured image to the display in the event that the characteristic does not satisfy the predetermined condition.

17. The endoscope system according to claim 1, wherein, after the characteristic satisfies the predetermined condition and then stops satisfying the predetermined condition, the circuitry is to control the focus of the endoscope system in the second manner gradually.

18. A non-transitory computer readable medium having stored thereon a program that, when executed by a computer, causes the computer to execute processing, the processing comprising:

monitoring a characteristic of an insertion portion that is to be inserted in and removed from a living body, the insertion portion to be connected to an image sensor that generate an image in a medical imaging system;

comparing the characteristics to a predetermined condition;

in response to the characteristic satisfying the predetermined condition, controlling a focus of the medical imaging system in a first manner and outputting a first captured image obtained by the imaging sensor just prior to the characteristic satisfying the predetermined condition; and in response to the characteristic not satisfying the predetermined condition, controlling the focus of the medical imaging system in a second manner, different from the first manner, stopping outputting of the first captured image, and outputting a real-time captured image.

19. A method, comprising:

monitoring a characteristic of an insertion portion that is to be inserted in and removed from a living body, the insertion portion to be connected to an image sensor that generates an image in a medical imaging system;

comparing the characteristics to a predetermined condition, wherein the predetermined characteristic is a fluctuation of luminance in a peripheral portion of the image within a predetermined period of time;

in response to the characteristic satisfying the predetermined condition, controlling a focus of the medical imaging system in a first manner; and in response to the characteristic not satisfying the predetermined condition, controlling the focus of the medical imaging system in a second manner, different from the first manner.

20. The method according to claim 19, wherein the first manner includes auto focusing the focus of the medical imaging system.

* * * * *